(12) United States Patent
Nakamoto et al.

(10) Patent No.: US 10,792,048 B2
(45) Date of Patent: Oct. 6, 2020

(54) HEMOSTASIS TOOL

(71) Applicant: TERUMO KABUSHIKI KAISHA, Shibuya-ku, Tokyo (JP)

(72) Inventors: Ryo Nakamoto, Hiratsuka (JP); Teppei Hayashi, Fujinomiya (JP); Takatsugu Yamaguchi, Fujinomiya (JP); Junichi Kobayashi, Fuji (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 547 days.

(21) Appl. No.: 15/225,008

(22) Filed: Aug. 1, 2016

(65) Prior Publication Data

US 2016/0338710 A1 Nov. 24, 2016

Related U.S. Application Data

(63) Continuation of application No. PCT/JP2015/050923, filed on Jan. 15, 2015.

(30) Foreign Application Priority Data

Feb. 17, 2014 (JP) ................................ 2014-028019

(51) Int. Cl.
*A61B 17/132* (2006.01)
*A61B 17/135* (2006.01)
*A61B 90/00* (2016.01)

(52) U.S. Cl.
CPC ........ *A61B 17/1325* (2013.01); *A61B 17/135* (2013.01); *A61B 2090/037* (2016.02); *A61B 2090/0807* (2016.02)

(58) Field of Classification Search
CPC ................ A61B 17/132; A61B 17/135; A61B 2090/037; A61B 5/022; A61B 17/1322;
(Continued)

(56) References Cited

U.S. PATENT DOCUMENTS 4,260,179 A * 4/1981 Yamaguchi ........... C07C 317/00
427/150
4,397,483 A * 8/1983 Hiraishi ................. B41M 5/124
427/150

(Continued)

FOREIGN PATENT DOCUMENTS

JP 5-172666 A 7/1993
JP 6-213738 A 8/1994
(Continued)

OTHER PUBLICATIONS

International Search Report (PCT/ISA/210) dated Apr. 21, 2015, by the Japanese Patent Office as the International Searching Authority for International Application No. PCT/JP2015/050923.

(Continued)

*Primary Examiner* — Darwin P Erezo
*Assistant Examiner* — Christian D Knauss
(74) *Attorney, Agent, or Firm* — Buchanan Ingersoll & Rooney PC

(57) ABSTRACT

A hemostasis tool has a flexible bandage body that is used by being wound around a puncture site, a balloon that is arranged in the bandage body, and that is dilated by injecting a fluid so as to compress the puncture site in a dilated state, and a detection unit that detects a strength level of a pressing force of the balloon pressing the puncture site, based on discoloration or deformation. In this manner, it is possible to detect the pressing force of the balloon pressing the puncture site. Accordingly, the balloon can properly compress the puncture site.

10 Claims, 10 Drawing Sheets

(58) Field of Classification Search
CPC ............ A61B 17/1325; A61B 17/1327; A61B 17/1355; B41M 5/165
See application file for complete search history.

(56) References Cited

U.S. PATENT DOCUMENTS

| | | | | | |
|---|---|---|---|---|---|
| 4,776,331 | A | * | 10/1988 | Simjian | A61F 15/00 116/270 |
| 4,903,991 | A | * | 2/1990 | Wright | B42D 25/29 283/70 |
| 5,263,966 | A | * | 11/1993 | Daneshvar | A61F 5/34 606/201 |
| 5,423,852 | A | * | 6/1995 | Daneshvar | A61B 17/135 128/118.1 |
| 5,667,524 | A | * | 9/1997 | Bourgeois, Jr. | A61B 17/135 606/202 |
| 5,942,464 | A | * | 8/1999 | Vaughn | B41M 5/165 427/150 |
| 2004/0098035 | A1 | * | 5/2004 | Wada | A61B 17/1325 606/201 |
| 2012/0116444 | A1 | | 5/2012 | Zodnik et al. | |

FOREIGN PATENT DOCUMENTS

| | | |
|---|---|---|
| JP | 2000-515773 A | 11/2000 |
| WO | WO 97/02783 A1 | 1/1997 |
| WO | WO 2011/096336 A1 | 8/2011 |

OTHER PUBLICATIONS

Written Opinion (PCT/ISA/237) dated Apr. 21, 2015, by the Japanese Patent Office as the International Searching Authority for International Application No. PCT/JP2015/050923.

* cited by examiner

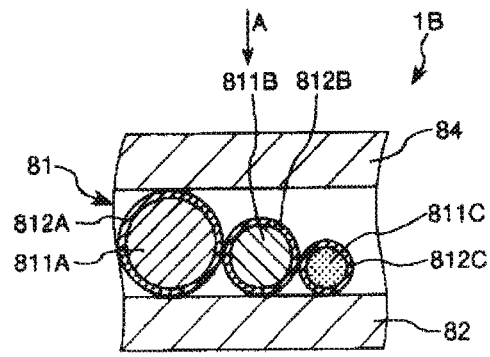 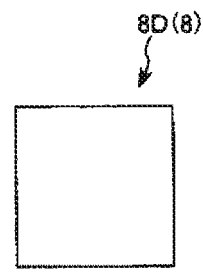
FIG. 9(a)    FIG. 9(b)
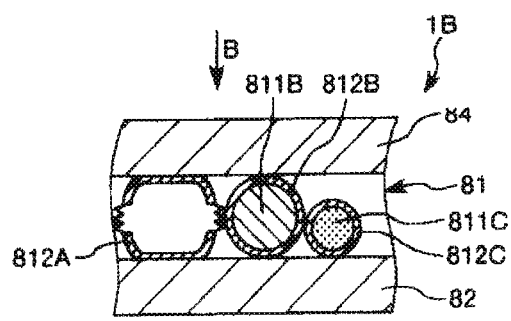 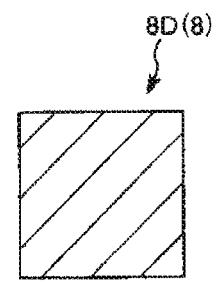
FIG. 10(a)    FIG. 10(b)
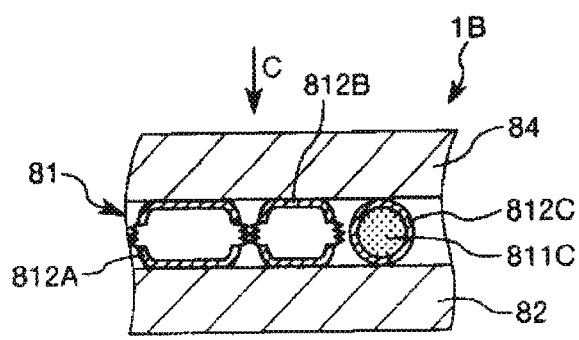 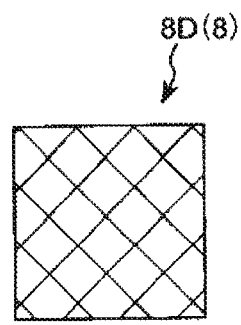
FIG. 11(a)    FIG. 11(b)

HEMOSTASIS TOOL

CROSS-REFERENCES TO RELATED APPLICATIONS

This application is a continuation of International Application No. PCT/JP2015/050923 filed on Jan. 15, 2015, and claims priority to Japanese Patent Application No. 2014-028019 filed on Feb. 17, 2014, the entire content of each of which is incorporated herein by reference.

TECHNICAL FIELD

The present invention relates to a hemostasis tool.

BACKGROUND DISCUSSION

Known methods of treatment, inspection, or the like involve percutaneously inserting a catheter into a blood vessel. After the catheter is removed, it is necessary to perform hemostasis on the puncture site. A known hemostasis tool for performing hemostasis is used by being mounted on an arm or a leg of the patient. In particular, the hemostasis tool is wound around a portion of the patient's arm or leg having the puncture site requiring hemostasis so as to compress the puncture site. Such a hemostasis tool is disclosed in JP-T-2000-515773 and includes a bandage body wound around a limb of the arm or the leg having the puncture site, and a balloon installed inside the bandage body so as to be capable of dilating and deflating. The balloon in a dilated state can compress the puncture site requiring hemostasis. The hemostasis tool configured in this way can perform hemostasis on the puncture site by pressing the puncture site with a suitably strong pressing force of the balloon.

However, according to the hemostasis tool disclosed in JP-T-2000-515773, it is difficult to determine whether or not the pressing force is suitable when the balloon presses the puncture site requiring hemostasis. In a case where the pressing force of the balloon is weaker than necessary, the hemostasis is insufficiently performed. On the other hand, in a case where the pressing force of the balloon is stronger than necessary, there is a possibility that the limb may be excessively compressed depending on a strength level thereof. In view of these circumstances, it is conceivable to adopt a configuration in which the above-described hemostasis tool includes a pressure gauge. However, the overall hemostasis tool will then increase in size and/or in weight, and so may become difficult for a user or an operator to use and more burdensome to a patient.

SUMMARY

An object of the present disclosure is to provide a hemostasis tool which can properly press a site requiring hemostasis without unduly troubling a user or placing an undue burden on a patient. These and other objects can be achieved by the following configurations.

A hemostasis tool has a flexible bandage body that is used by being wound around a site requiring hemostasis, at least one balloon that is arranged in the bandage body, and that is dilated by injecting a fluid so as to compress the site requiring hemostasis in a dilated state thereof, and a detection unit that detects a strength level of a pressing force of the balloon pressing the site requiring hemostasis, based on discoloration or deformation.

In the hemostasis tool according to the above-described configuration (1), the bandage body has a light-transmitting portion having light transmittance. The detection unit is located between the balloon and the light-transmitting portion, and is visible via the light-transmitting portion.

In the hemostasis tool according to the above-described configuration, the detection unit has a discoloration portion which is irreversibly discolored due to an increase in the pressing force.

In the hemostasis tool according to the above-described configuration, the discoloration portion has a color developer, a developer which develops a color of the color developer by acting on the color developer, and a partition wall portion which separates the color developer and the developer, and which is broken due to the increase in the pressing force.

In the hemostasis tool according to the above-described configuration, the partition wall portion has a portion whose breaking limit is different.

In the hemostasis tool according to any one of the above-described configurations, the detection unit has a deformation portion which is deformed in response to the strength of the pressing force, and which detects the strength level of the pressing force, based on a deformation amount thereof.

In the hemostasis tool according to the above-described configuration, the deformation portion is arranged so as to face the light-transmitting portion, and dilates in a plane direction of the bandage body in response to the strength of the pressing force.

The hemostasis tool according to the above-described configuration has a scale or a marker that indicates the strength level of the pressing force in response to the deformation amount of the deformation portion.

In the hemostasis tool according to any one of the above-described configurations, the detection unit is arranged at a position shifted from a straight line passing through the center of the balloon in the dilated state and the site requiring hemostasis.

In the hemostasis tool according to any one of the above-described configurations, the detection unit is flexible, and has a pair of pinching pieces which pinch the detection unit and which are harder than the detection unit.

According to the present disclosure, a detection unit can detect a pressing force of a balloon pressing a site requiring hemostasis. Therefore, the balloon can properly compress the site requiring hemostasis.

BRIEF DESCRIPTION OF DRAWINGS

FIG. 9(a) is an enlarged sectional view illustrating a discoloration portion included in a third embodiment of a hemostasis tool according to the present disclosure, and FIG. 9(b) is a view when viewed in a direction of an arrow A in FIG. 9(a).

FIG. 10(a) is an enlarged sectional view illustrating a process in which the discoloration portion included in the third embodiment of the hemostasis tool according to the present disclosure is discolored, and FIG. 10(b) is a view when viewed in a direction of an arrow B in FIG. 10(a).

FIG. 11(a) is an enlarged sectional view illustrating a process in which the discoloration portion included in the third embodiment of the hemostasis tool according to the present disclosure is discolored, and FIG. 11(b) is a view when viewed in a direction of an arrow C in FIG. 11(a).

DETAILED DESCRIPTION

Hereinafter, a hemostasis tool according to the present disclosure will be described with reference to preferred embodiments illustrated in the accompanying drawings.

Figure 1:
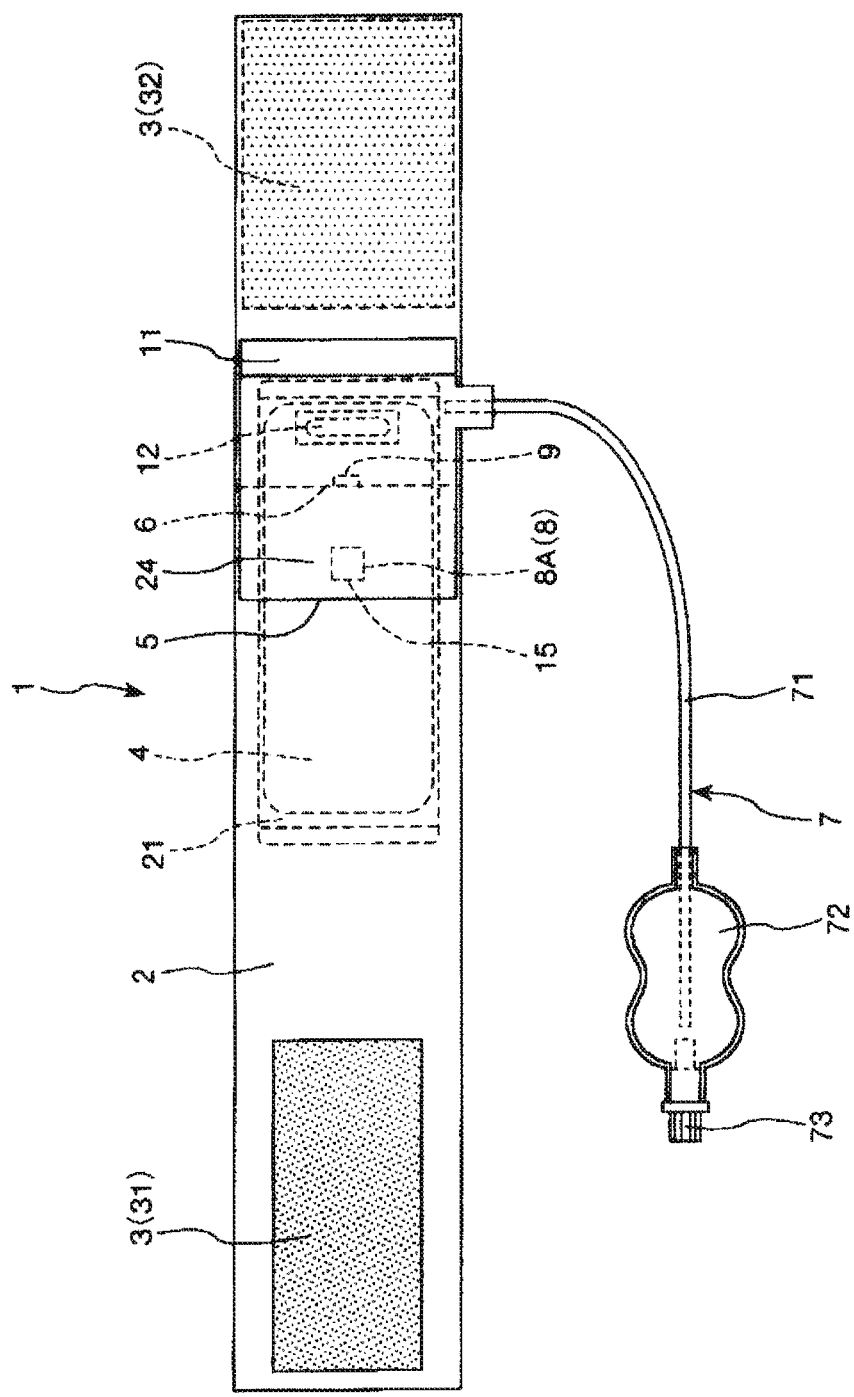
FIG. 1 is a bottom view illustrating a first embodiment of a hemostasis tool, in a state where an inner surface side is visible when the hemostasis tool is mounted on a wrist, according to the present disclosure.
Figure 2:
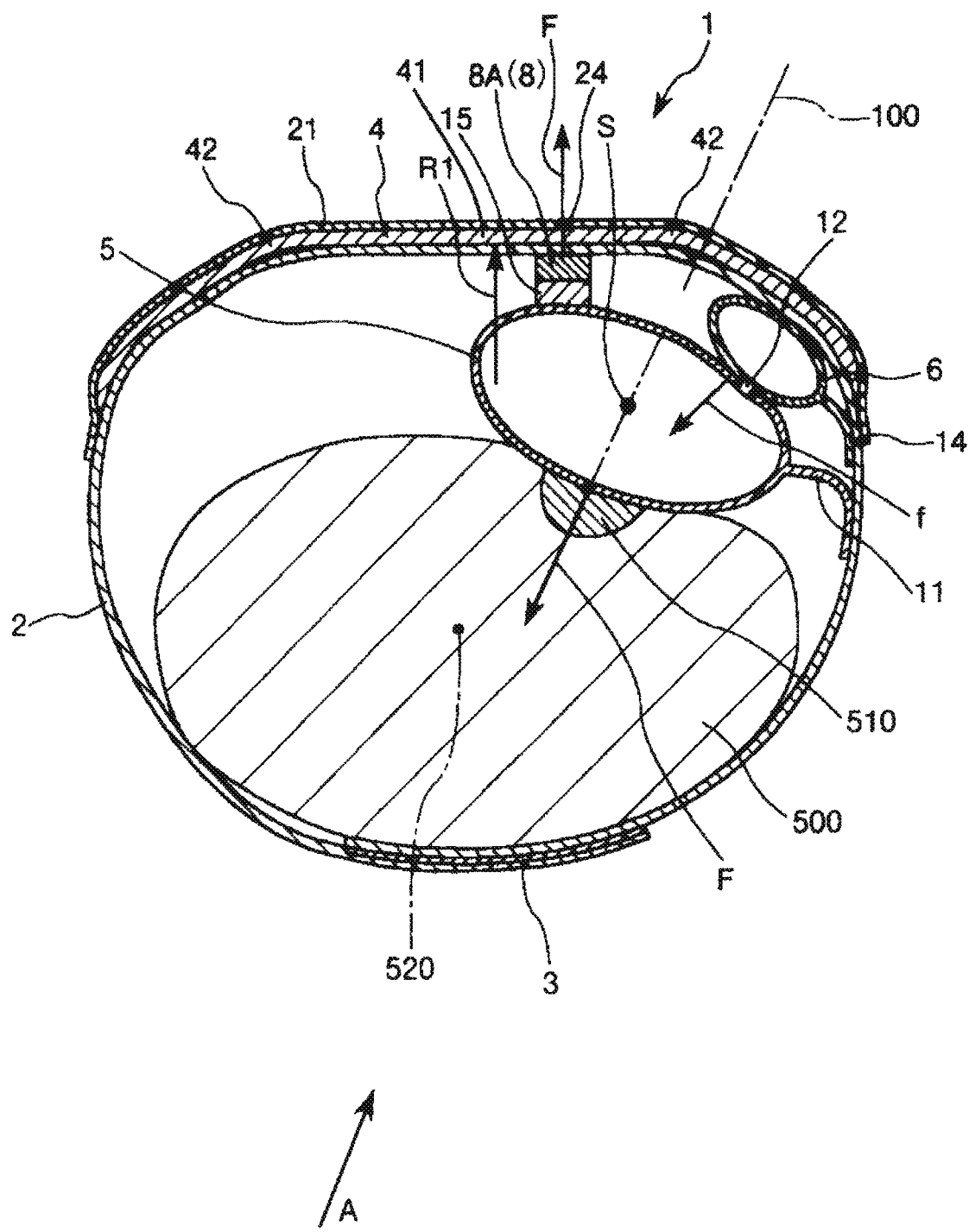
FIG. 2 is a sectional view illustrating a use state of the hemostasis tool illustrated in FIG. 1.

FIG. 1 is a bottom view illustrating a first embodiment of a hemostasis tool in a state where an inner surface side is visible when the hemostasis tool is mounted on a wrist. FIG. 2 is a sectional view illustrating a use state of the hemostasis tool illustrated in FIG. 1. FIGS. 3(a), 3(b), and 3(c) are enlarged and detailed sectional views illustrating a discoloration portion included in the hemostasis tool illustrated in FIG. 1.

A hemostasis tool 1 illustrated in FIGS. 1 and 2 includes a bandage body 2 that is wound around a wrist 500 (or other limb portion) at a puncture site 510 after removal of a catheter or the like which had been percutaneously inserted into an artery through a puncture hole or other wound) at the puncture site 510. The hemostasis tool 1 also includes a hook-and-loop fastener 3 serving as fixing means for fixing the bandage body 2 and the wrist 500 in a state the bandage body 2 is wounded and mounted thereon, a reinforcement plate 4, a balloon 5, an auxiliary balloon (balloon) 6, a detection unit 8, and a support piece 15 that supports the detection unit 8.

The bandage body 2 is a flexible and band-shaped member. As illustrated in FIG. 2, the bandage body 2 is wound so as to turn around the outer periphery of the wrist 500, and is mounted on the wrist 500 by overlapping portions in the vicinity of both ends with each other. Then, in the bandage body 2, the overlapping portions are fixedly joined by the hook-and-loop fastener 3 (to be described later).

As a material of the bandage body 2, it is preferable to use soft plastic. For example, the material can include polyolefin such as polyvinyl chloride, polyethylene, polypropylene, polybutadiene, and ethylene-vinyl acetate copolymer (EVA), polyester such as polyethylene terephthalate (PET) and polybutyleneterephthalate (PBT), various thermoplastic elastomers such as polyvinylidene chloride, silicone, polyurethane, polyamide elastomer, polyurethane elastomer, polyester elastomer, and the like, or any optional combination thereof (blend resins, polymer alloys, laminates, or the like).

In addition, it is preferable that the bandage body 2 is substantially transparent, that is, the bandage body 2 has light transmittance. In this manner, a target lesion is visible from the outside. In the present embodiment, the bandage body 2 is entirely a light-transmitting portion.

A reinforcement plate holding portion 21 which holds a reinforcement plate 4 (to be described later) is formed in the central portion of the bandage body 2. The reinforcement plate holding portion 21 has a dual structure in which a separate band-shaped member is joined to an outer surface side (or an inner surface side) by using a fusion method (such as heat-welding, high frequency fusion, ultrasonic fusion, or the like) or by using an adhesion method (such as adhesion using an adhesive or a solvent), for example. The reinforcement plate holding portion 21 holds the reinforcement plate 4 inserted into a gap therebetween.

A male side (or a female side) 31 of the hook-and-loop fastener 3 which is generally called a Magic Tape (Registered Trademark) is fixedly installed on an inner surface side (front side of the paper surface in FIG. 1) of a portion of the bandage body 2, in the vicinity of the left end in FIG. 1. A female side (or a male side) 32 of the hook-and-loop fastener 3 is fixedly installed on an outer surface side (rear side of the paper surface in FIG. 1) of a portion of the bandage body 2, in the vicinity of the right end in FIG. 1. As illustrated in FIG. 2, the male side 31 and the female side 32 of the hook-and-loop fastener 3 are joined to each other, thereby mounting the bandage body 2 on the wrist 500. Note that, means for fixing a state where the bandage body 2 is wound around the wrist 500 is not limited to the hook-and-loop fastener 3. For example, snaps, buttons, clips, a frame member passing an end portion of the bandage body 2 therethrough, or the like may be employed.

The reinforcement plate 4 is inserted into a portion between the reinforcement plate holding portions 21 formed in a dual structure of the bandage body 2, thereby being supported by the bandage body 2.

The reinforcement plate 4 has a shape in which at least a portion thereof is curved toward the inner peripheral side. The reinforcement plate 4 is configured to include a material which is harder than that of the bandage body 2 and a discoloration portion 8A (to be described later), and maintains a substantially constant shape. Therefore, a portion of the bandage body 2 is reinforced. Hereinafter, the reinforced portion of the bandage body 2 is referred to as a "reinforcement portion 24".

As illustrated in FIG. 1, in the present embodiment, the reinforcement plate 4 has a shape which is relatively long in a longitudinal direction of the bandage body 2. As illustrated in FIG. 2, a central portion 41 in the longitudinal direction of the reinforcement plate 4 has a flat plate shape which is slightly curved. Curved portions 42 which are respectively curved toward the inner peripheral side and along the longitudinal direction of the bandage body 2 (circumferential direction of the wrist 500) are formed on both sides of the central portion 41. That is, a radius of curvature R1 of the curved portion 42 is smaller than a radius of curvature R1 of the central portion 41 (in the illustrated configuration, R1 is substantially infinite). In addition, in the present embodiment, the reinforcement plate 4 has the a curved shape, but may instead be flat.

As a material of the reinforcement plate 4, it is preferable to use rigid plastic. For example, the material can include polyolefin such as acrylic resins, polyvinyl chloride (particularly rigid polyvinyl chloride), polyethylene, polypropylene, and polybutadiene, polyester such as polystyrene, poly-(4-methylpentene-1), polycarbonate, ABS resins, polymethyl methacrylate (PMMA), polyacetal, polyarylate, polyacrylonitrile, polyvinylidene fluoride, ionomers, acrylonitrile-butadiene-styrene copolymers, polyethylene terephthalate (PET), and polybutylene terephthalate (PBT), or fluorine-based resins such as butadiene-styrene copolymers, aromatic or aliphatic polyamide, polytetrafluoroethylene, and the like.

In addition, it is preferable that the reinforcement plate 4 is substantially transparent. In this manner, a target lesion is visible from the outside.

The reinforcement plate 4 configured as described above concentrates a pressing force F of the balloon 5 on the wrist side. That is, the reinforcement plate 4 has a function of assisting pressing pressure of the balloon 5.

The balloon 5 configured to include a flexible material is installed inside the reinforcement plate 4 and thus inside the bandage body 2. As illustrated in FIG. 2, the balloon 5 is dilated by injecting a predetermined amount (for example, 18 cc) of a fluid (gas such as air or a liquid). In a dilated state thereof, a portion of the balloon 5 is assigned to a puncture site 510 of the wrist 500 so as to compress the puncture site 510.

The balloon 5 is offset to one end side in the longitudinal direction of the reinforcement plate 4. That is, in the illustrated configuration, the balloon 5 is located so as to overlap substantially the right half side of the reinforcement plate 4 in FIG. 2.

A material of the balloon 5 is not particularly limited as long as the material is flexible. For example, it is possible to use a material which is the same as the material of the above-described bandage body 2. It is preferable that the balloon 5 is configured to include a material which has the same quality or the same type as that of the bandage body 2. In this manner, the balloon 5 can be easily joined to the bandage body 2 by means of fusion, and can be easily manufactured.

In addition, it is preferable that the balloon 5 is substantially transparent. In this manner, a target lesion is visible from the outside.

For example, a structure of the balloon 5 can be formed in a bag shape in which edge portions of a sheet member formed of the above-described material are sealed by using a fusion method, an adhesion method, or the like. In the illustrated configuration, the balloon 5 has a substantially square shape in a state where the balloon 5 is not dilated.

This balloon 5 is interlocked with the bandage body 2 via a flexible interlock portion 11. In the present embodiment, in the balloon 5, the side corresponding to the offset direction relative to the reinforcement plate 4, that is, only the right side in FIG. 2, is interlocked with the bandage body 2 via the interlock portion 11. A substantial length of the interlock portion 11 is relatively short. In this manner, the balloon 5 is arranged and fixed at the position offset relative to the reinforcement plate 4. It is preferable that the interlock portion 11 is configured to include a material which is the same as that of the balloon 5.

In the present embodiment, only one side of the balloon 5 is interlocked with the bandage body 2 by the interlock portion 11. In this manner, the balloon 5 adopts a slightly tilted posture in a state illustrated in FIG. 2. As a result, the pressing force F is applied to the puncture site 510 in a tilted direction.

As illustrated in FIG. 1, an injection unit 7 for injecting the fluid into the balloon 5 is connected to the balloon 5. A proximal portion of the injection unit 7 is connected to the balloon 5, and is configured to include a flexible tube 71 whose lumen communicates with the inside of the balloon 5, a bag body 72 installed in a distal portion of the tube 71, and a tubular connector 73 joined to the bag body 72.

When the balloon 5 is dilated (inflated), a distal projection portion of a syringe (not illustrated) is inserted into the connector 73. A plunger of the syringe is pushed so as to inject the fluid inside the syringe into the balloon 5 via the injection unit 7. If the distal projection portion of the syringe is removed from the connector 73 after the fluid is injected into the balloon 5, a check valve incorporated in the connector 73 is closed so as to prevent the fluid from leaking out. In this manner, the dilated state of the balloon 5 is maintained.

As illustrated in FIG. 2, an auxiliary balloon 6 configured to include a flexible material is installed between the reinforcement plate 4 and the balloon 5. The auxiliary balloon 6 entirely or partially overlaps the balloon 5 along a thickness direction of the bandage body 2, and has a function as a pressing member for pressing the balloon 5.

The auxiliary balloon 6 is interlocked with the bandage body 2 via a flexible interlock portion 14. In the present embodiment, similarly to the balloon 5, in the auxiliary balloon 6, a side corresponding to the offset direction relative to the reinforcement plate 4, that is, only the right side in FIG. 2, is interlocked with the bandage body 2 via the interlock portion 14.

A positioning marker 9 is arranged in an end portion of the auxiliary balloon 6 which is located on a side opposite to the interlock portion 14, as shown in FIG. 1. As will be described later, the marker 9 is aligned with the puncture site 510, and the bandage body 2 is wound and fixed. In this manner, the balloon 5 can be easily positioned in the puncture site 510. Note that, unlike the illustrated configuration, the marker 9 may be disposed in the central portion of the balloon 5.

As illustrated by an arrow f in FIG. 2, the pressure of the fluid filling the inside causes the auxiliary balloon 6 to press the balloon 5 in a direction toward substantially a center 520 of the wrist 500. The pressing force is received from the auxiliary balloon 6. In this manner, as illustrated by an arrow F in FIG. 2, the balloon 5 presses (compresses) the puncture site 510 in the tilting direction (direction toward the center 520 of the wrist 500) rather than in the perpendicular direction from above to below (direction perpendicular to the surface of the wrist 500). In this manner, compared to a case where the puncture site 510 is pressed (compressed) in the perpendicular direction from above to below, an improved hemostasis effect can be obtained, and hemostasis can be more reliably performed.

In the illustrated configuration, in a state illustrated in FIG. 2, the balloon 5 is not in contact with the reinforcement plate 4 (via the bandage body 2). However, a portion of the balloon 5 may be in contact with the reinforcement plate 4 (via the bandage body 2).

A material of the auxiliary balloon 6 is not particularly limited. For example, it is possible to use a material which is the same as the material of the above-described bandage body 2. In addition, it is preferable that the auxiliary balloon 6 is substantially transparent. In this manner, a target lesion is visible from the outside. In addition, a structure of the auxiliary balloon 6 can employ the same structure as the balloon 5.

In the present embodiment, the width of the auxiliary balloon 6 in the longitudinal direction of the bandage body 2 is set to be smaller than that of the balloon 5. In this manner, the size of the auxiliary balloon 6 is set to be smaller than that of the balloon 5, thereby locally pressing the balloon 5. In this manner, the direction of the pressing force F applied from the balloon 5 to the puncture site 510 can be more reliably tilted.

In addition, in the present embodiment, the auxiliary balloon 6 is located in the vicinity of the right end portion in FIG. 2 in the longitudinal direction of the reinforcement plate 4. In this manner, the direction of the pressing force f applied from the auxiliary balloon 6 to the balloon 5 can be more reliably oriented in the direction toward the center 520 of the wrist 500. As a result, the direction of the pressing force F applied from the balloon 5 to the puncture site 510 can be more reliably tilted.

In addition, in the present embodiment, a portion of the balloon 5 and a portion of the auxiliary balloon 6 are joined to each other by using a fusion method or an adhesion method. Then, a joint portion therebetween has a communicating portion (opening portion) 12 which communicates with the inside of the balloon 5 and the inside of the auxiliary balloon 6. In this manner, if the fluid is injected into the balloon 5 as described above, the injected fluid partially flows into the auxiliary balloon 6 via the communicating portion 12. In response to the dilated balloon 5, the auxiliary balloon 6 is dilated. In this manner, both of these can be dilated by a single operation, thereby providing excellent operability.

As described above, the hemostasis tool 1 has the detection unit 8. As illustrated in FIG. 2, the detection unit 8 is disposed between the balloon 5 and the reinforcement plate 4 (bandage body 2). The detection unit 8 has a function to detect strength level of the pressing force F of the balloon 5 which is applied to the puncture site 510.

Figure 3:
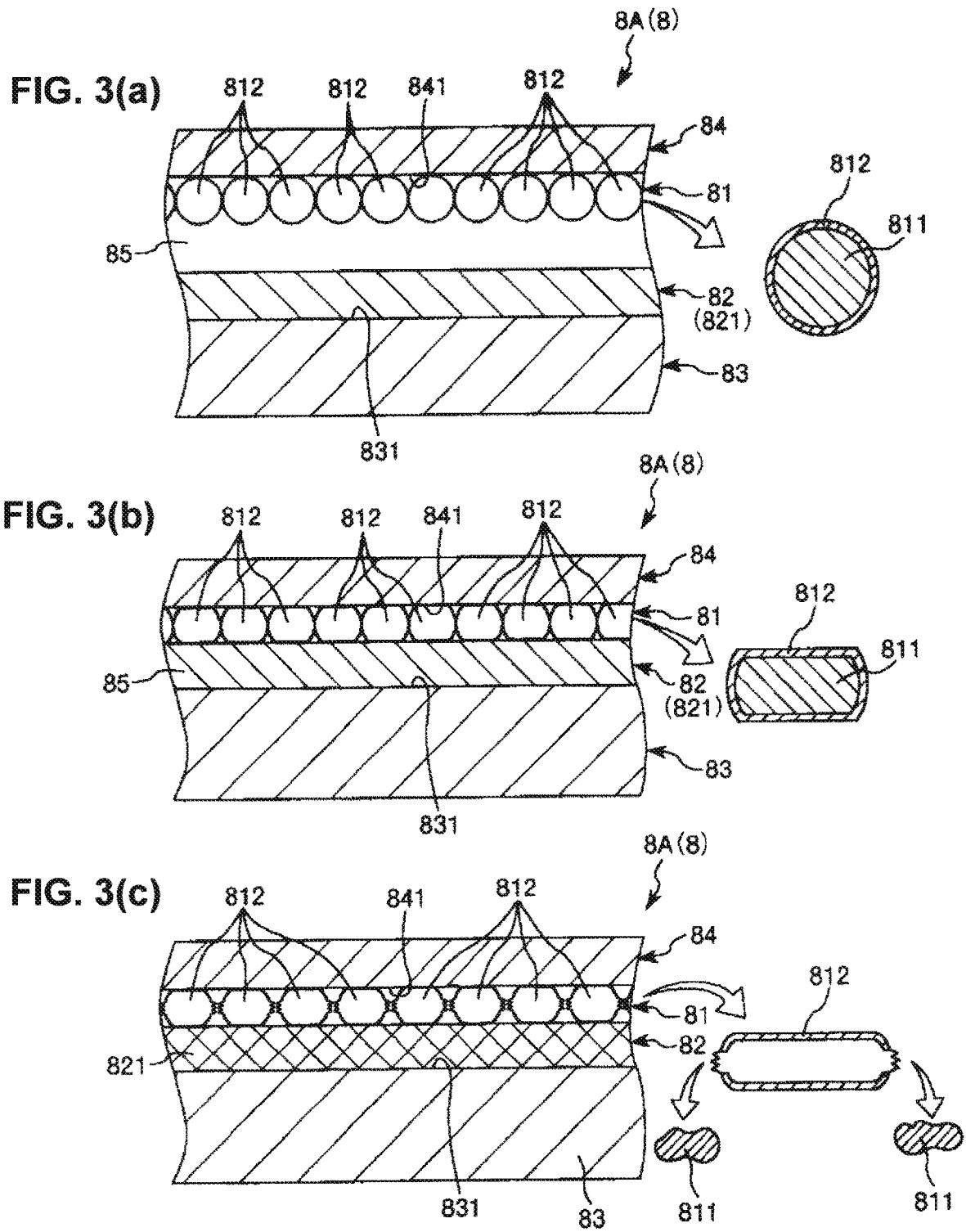
FIGS. 3(a), 3(b), and 3(c) are enlarged and detailed sectional views illustrating a discoloration portion included in the hemostasis tool illustrated in FIG. 1.

As illustrated in FIGS. 1 to 3, the detection unit 8 is configured to include the discoloration portion 8A which is discolored when the pressing force F applied from the balloon 5 to the puncture site 510 increases and the pressing force F reaches a first predetermined pressing force F1. According to this configuration, the detection unit 8 realizes that the strength level of the pressing force F is visualized.

In the present embodiment, the first predetermined pressing force F1 represents a value which is slightly higher than a value of the strength level which enables sufficient hemostasis to be performed on the puncture site 510. Specifically, the first predetermined pressing force F1 is set to pressure which is slightly higher than a patient's blood pressure (systolic blood pressure), and a value of the strength level which enables the whole area of the puncture site 510 to be pressed. The first predetermined pressing force F1 can be known by measuring the patient's blood pressure before the hemostasis tool 1 is used.

Hereinafter, the discoloration portion 8A will be described in detail.

As illustrated in FIGS. 3(a) to 3(c), the discoloration portion 8A has a first support layer 83, a developer layer 82, a color developer layer 81, and a second support layer 84 which are sequentially stacked from the lower side.

The first support layer 83 and the second support layer 84 respectively have a substantially rectangular shape in a plan view. In addition, the first support layer 83 and the second support layer 84 are arranged to face each other, and respective edge portions thereof are joined to each other by means of fusion, for example. Accordingly, an air layer 85 is formed between the first support layer 83 and the second support layer 84.

The color developer layer 81 is disposed on an inner side surface 841 of the second support layer 84. The color developer layer 81 has multiple microcapsules (partition wall portions) 812 and a color developer 811 included in the respective microcapsules 812.

The respective microcapsules 812 have a spherical shape, and are configured to include a shell whose wall thickness is constant. The respective microcapsules 812 are held densely on one surface of the first support layer 83, that is, side by side so that the adjacent microcapsules 812 are in contact with each other. In addition, in a natural state, the respective microcapsules 812 hold the color developer 811 in a liquid-tight manner. If an external force is applied and reaches a breaking limit, the respective microcapsules 812 are broken. Due to this breaking, the color developer 811 included therein flows out from the respective microcapsules 812.

In addition, for example, the respective microcapsules 812 are fixed to and held by the second support layer 84 via an adhesive layer or the like (not illustrated).

A material of the microcapsule 812 is not particularly limited. For example, it is possible to use a water-insoluble and oil-insoluble resin material such as polyurethane resins and the like.

The color developer 811 is configured to include a colorless and transparent liquid. The color developer 811 comes into contact with the developer 821 of the developer layer 82, and the developer 821 acts on the color developer 811. In this manner, the color developer 811 is discolored from colorless to red. Note that, the color developer 811 is irreversibly discolored. That is, if the color developer 811 is discolored once to red, the color developer 811 is prevented from being discolored again to colorless.

A material of the color developer 811 is not particularly limited. However, it is possible to preferably use an electron-donating dye. For example, the electron-donating dye includes triphenylmethane phthalide-based compounds, fluoran-based compounds, phenothiazine-based compounds, indolyl phthalide-based compounds, leuco auramine-based compounds, rhodamine lactam-based compounds, triphenylmethane-based compounds, diphenylmethane-based compounds, triazene-based compounds, spiropyran-based compounds, fluorene-based compounds, and the like. In addition, it is possible to set a color of the color developer 811 after color development by changing a functional group of these compounds. In the present embodiment, the color developer 811 is configured to include a compound showing a red color after the color developer 811 is discolored.

The developer layer 82 is disposed on an inner side surface 831 of the first support layer 83. The developer layer 82 includes the developer 821 which develops the color developer 811 by acting on the color developer 811. The developer layer 82 is obtained by applying the developer 821 onto one side surface of the second support layer 84.

A material of the developer 821 is not particularly limited. For example, it is possible to use clay materials such as acid clay, activated clay, attapulgite, zeolite, bentonite, kaolin, and the like, metal salts of aromatic carboxylic acid, phenol-formaldehyde resins, or the like.

In addition, a material of the first support layer 83 and the second support layer 84 is not particularly limited. For example, it is possible to use various resin materials such as polyethylene terephthalate.

In addition, as illustrated in FIG. 2, the support piece 15 is disposed between the balloon 5 and the discoloration portion 8A. The support piece 15 is configured to include a material which is harder than that of the discoloration portion 8A, and an upper surface side thereof supports the discoloration portion 8A. According to this configuration, the discoloration portion 8A is in a state of being pinched between the support piece 15 and the reinforcement portion 24 which are harder than the discoloration portion 8A. Therefore, the pressing force F is reliably transmitted to the discoloration portion 8A. In this manner, in the present embodiment, the support piece 15 and the reinforcement portion 24 configure a pair of pinching pieces.

In addition, the support piece 15 is large enough to include the discoloration portion 8A in a plane view of the discoloration portion 8A. Furthermore, the reinforcement plate 4 is sufficiently larger than the discoloration portion 8A in the plane view of the discoloration portion 8A. For these reasons, the pressing force F is substantially uniformly applied to the entire surface of the discoloration portion 8A.

Note that, it is preferable that the support piece 15 and the balloon 5 are fixed to each other via an adhesive, for example. In addition, it is preferable that the support piece 15 and the discoloration portion 8A are fixed to each other via an adhesive, for example.

As illustrated in FIG. 2, if the balloon 5 in a mounted state is dilated, the puncture site 510 is compressed by the pressing force F of the balloon 5. On the other hand, the discoloration portion 8A is compressed via the support piece 15 by the balloon 5 compressing the puncture site 510. Accordingly, the discoloration portion 8A is pressed against the reinforcement portion 24 of the bandage body 2 by the pressing force F. At this time, the discoloration portion 8A in a state where the color developer layer 81 and the developer layer 82 are separated from each other (refer to FIG. 3(a)) is brought into a state where the color developer layer 81 and the developer 821 move close to and come into contact with each other. If the balloon 5 is further dilated in this state, as illustrated in FIG. 3(b), the discoloration portion 8A is pressed between the reinforcement portion 24 and the support piece 15, thereby deforming and crushing the respective microcapsules 812. Then, as illustrated in FIG. 3(c), if the pressing force F reaches the first predetermined pressing force F1, the respective microcapsules 812 eventually reach the breaking limit, and are broken. Due to this breaking, the color developer 811 flows out from the respective microcapsules 812, and the color developer 811 is provided for (supplied to) the developer layer 82. As a result, the developer 821 acts on the color developer 811, and the color developer 811 is discolored to red. This discoloration is visible via the bandage body 2. In this manner, a user or an operator can recognize that the strength level of the pressing force F applied from the balloon 5 to the puncture site 510 reaches the first predetermined pressing force F1. Then, it is possible to adjust the pressing force F applied from the balloon 5 to the puncture site 510 so as to have suitable strength by stopping the supply of the fluid to the balloon 5. Accordingly, the balloon 5 can properly compress the puncture site 510.

Furthermore, as described above, the discoloration portion 8A is irreversibly discolored. Accordingly, a user can obviously and reliably recognize that the discoloration portion 8A is discolored.

Here, as illustrated in FIG. 2, if the puncture site 510 is viewed in a direction of a straight line 100 passing through a center S of the balloon 5 in a dilated state and the puncture site 510, it is easy to confirm whether or not hemostasis is performed on the puncture site 510. In a case where the discoloration portion 8A is located on the straight line 100, the discoloration portion 8A overlaps the puncture site 510, and thus, visibility of the puncture site 510 is hindered. In addition, in order that both the discoloration portion 8A and the puncture site 510 are visible, it is necessary to change the orientation of the wrist (arm) or to change a point of view.

However, in the present embodiment, the discoloration portion 8A is located at a position shifted from the straight line 100. In this manner, it is possible to avoid the discoloration portion 8A from hindering the visibility of the puncture site 510. Accordingly, the discoloration portion 8A and the puncture site 510 can be concurrently visible in the direction of the straight line 100. Therefore, the orientation of the wrist may not be changed, or the point of view may not be changed. As a result, it is possible to stabilize the puncture site 510 as much as possible until hemostasis is completely performed on the puncture site 510. Accordingly, the hemostasis can be more quickly performed.

Next, a method of using the hemostasis tool 1 will be described.

[1] Before the hemostasis tool 1 is mounted on the wrist 500, the balloon 5 and the auxiliary balloon 6 are in a state where both of these are not dilated. In a case of the wrist 500, the puncture site 510 occurring in the artery is normally located at a position biased to the thumb side on the inner side (side having a tendon) of the wrist 500. While the puncture site 510 is compressed using the finger or the like, the balloon 5 is located on the puncture site 510. The bandage body 2 is wounded around the wrist 500, and the vicinity of both end portions of the bandage body 2 is fixed (joined) by the hook-and-loop fastener 3.

[2] If the hemostasis tool 1 is mounted on the wrist 500, a syringe (not illustrated) is connected to the connector 73 of the injection unit 7. In the above-described manner, the fluid is injected into the balloon 5 and the auxiliary balloon 6, thereby dilating the balloon 5 and the auxiliary balloon 6. Then, when the pressing force F applied from the balloon 5 to the puncture site 510 reaches the first predetermined pressing force F1, as described above, the microcapsule 812 of the discoloration portion 8A is broken, and the color developer 811 is supplied to the developer 821. In this manner, the discoloration portion 8A is discolored from colorless to red. This discoloration is visible via the bandage body 2 (curved portion 42). In this manner, it is possible to recognize that a value of the pressing force F applied from the balloon 5 to the puncture site 510 reaches a predetermined value.

[3] If it is confirmed that the discoloration portion 8A is discolored, the supply of the fluid to the balloon 5 is stopped, and the syringe is detached from the connector 73. In this manner, the balloon 5 and the auxiliary balloon 6 maintain a dilated state, thereby maintaining a state of compressing the puncture site 510 (refer to FIG. 2). In this manner, the more excellent hemostasis effect can be obtained, and the puncture site 510 can be properly compressed. Accordingly, it is possible to reliably prevent the hemostasis from being insufficiently performed, or to reliably prevent the hand from being numbed or suffering poor blood circulation due to excessive pressure.

Figure 4:
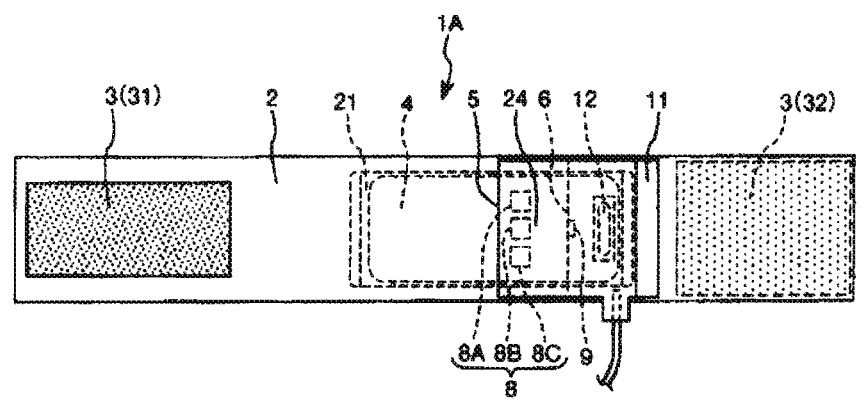
FIG. 4 is a bottom view illustrating a second embodiment of a hemostasis tool, in a state where an inner surface side is visible when the hemostasis tool is mounted on a wrist, according to the present disclosure.
Figure 5:
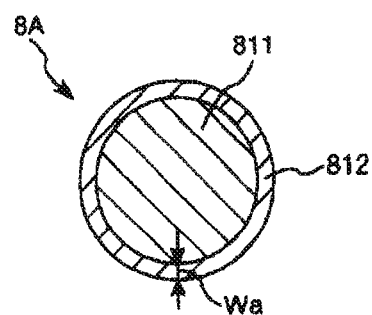
FIG. 5 is a sectional view illustrating a microcapsule belonging to a discoloration portion 8A included in the hemostasis tool illustrated in FIG. 4.
Figure 6:
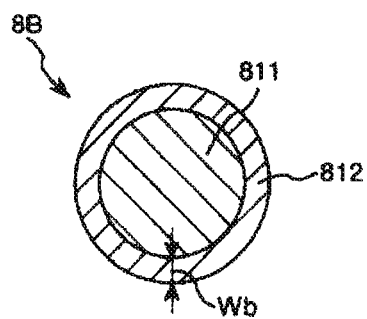
FIG. 6 is a sectional view illustrating a microcapsule belonging to a discoloration portion 8B included in the hemostasis tool illustrated in FIG. 4.
Figure 7:
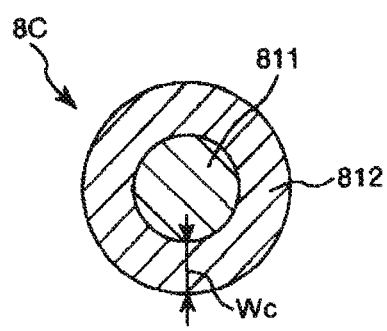
FIG. 7 is a sectional view illustrating a microcapsule belonging to a discoloration portion 8C included in the hemostasis tool illustrated in FIG. 4.

FIG. 4 is a bottom view illustrating a second embodiment of a hemostasis tool in a state where an inner surface side is visible when the hemostasis tool is mounted on the wrist. FIG. 5 is a sectional view illustrating a microcapsule belonging to the discoloration portion 8A included in the hemostasis tool illustrated in FIG. 4. FIG. 6 is a sectional view illustrating a microcapsule belonging to a discoloration portion 8B included in the hemostasis tool illustrated in FIG. 4. FIG. 7 is a sectional view illustrating a microcapsule belonging to a discoloration portion 8C included in the hemostasis tool illustrated in FIG. 4. FIGS. 8(a), (b), and (c) are plan views illustrating a process in which each discoloration portion illustrated in FIG. 4 is discolored.

Hereinafter, the second embodiment of the hemostasis tool according to the present disclosure will be described with reference to the drawings. However, points different from those in the above-described embodiment will be mainly described, and description of the same points will be omitted.

A hemostasis tool 1A according to the present embodiment is the same as that according to the first embodiment except that the installed number of the discoloration portions is different.

As illustrated in FIG. 4, the detection unit 8 of the hemostasis tool 1A has three discoloration portions 8A, 8B, and 8C. The discoloration portions 8A to 8C are arrayed along the width direction of the bandage body 2. In addition, the pressing forces F respectively applied to the discoloration portions 8A to 8C are substantially equal.

In addition, the discoloration portions 8A to 8C respectively have different breaking limits of the microcapsule 812. Specifically, as illustrated in FIGS. 5 to 7, a wall thickness Wa of each microcapsule 812 of the discoloration portion 8A, a wall thickness Wb of each microcapsule 812 of the discoloration portion 8B, and a wall thickness Wc of each microcapsule 812 of the discoloration portion 8C satisfy a relationship of Wa<Wb<Wc.

Each microcapsule 812 of the discoloration portion 8A is broken when the pressing force F reaches the first predetermined pressing force F1. Each microcapsule 812 of the discoloration portion 8B is broken when the pressing force F reaches a second predetermined_pressing force F2 which is greater than the first predetermined pressing force F1. Each microcapsule 812 of the discoloration portion 8C is broken when the pressing force F reaches a third predetermined pressing force F3 which is greater than the second predetermined_pressing force F2.

In the present embodiment, the first predetermined pressing force F1 has strength suitable for a patient whose blood pressure is 130 mmHg or lower. The second predetermined-_pressing force F2 has strength suitable for a patient whose blood pressure is 131 mmHg to 140 mmHg. The third predetermined pressing force F3 has strength suitable for a patient whose blood pressure is 141 mmHg to 150 mmHg.

Hereinafter, a method of using the hemostasis tool 1A will be described. Note that, a case will be described where a patient's blood pressure is 145 mmHg.

First, the patient's blood pressure is measured before the hemostasis tool 1A is brought into a mounted state. Since the patient's blood pressure is 145 mmHg, if the discoloration portion 8C is discolored, it is recognized whether the pressing force F reaches the third predetermined pressing force F3.

Then, the hemostasis tool 1A is brought into the mounted state, and the balloon 5 is gradually dilated. If the pressing force F increases and reaches the first predetermined pressing force F1, the microcapsule 812 of the discoloration portion 8A is broken. In this manner, as illustrated in FIG. 8(a), the discoloration portion 8A is discolored. If the balloon 5 is further dilated and the pressing force F reaches the second predetermined_pressing force F2, the microcapsule 812 of the discoloration portion 8B is broken. In this manner, as illustrated in FIG. 8(b), the discoloration portion 8B is also discolored subsequently to the discoloration portion 8A. Since it is visible that the discoloration portion 8B is discolored, it is possible to recognize that the pressing force F applied from the balloon 5 to the puncture site 510 is close to the third predetermined pressing force F3.

Then, the fluid is supplied to the balloon 5 little by little. That is, speed for operating a syringe (not illustrated) is reduced. In this manner, it is possible to reliably stop the supply of the fluid to the balloon 5 immediately after the discoloration portion 8C is discolored. Accordingly, it is possible to more reliably prevent the balloon 5 from excessively compressing the puncture site 510.

Figure 8C:
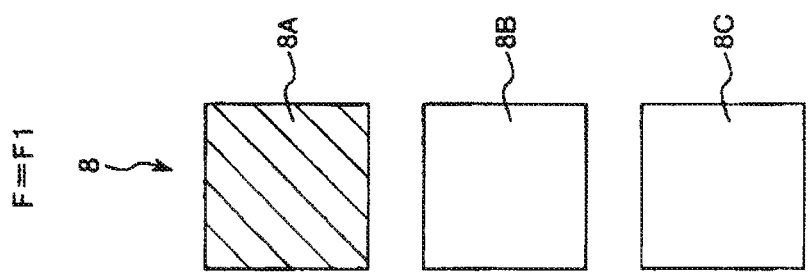
FIGS. 8(a), (b), and (c) are plan views illustrating a process in which each discoloration portion illustrated in FIG. 4 is discolored.
Figure 8B:
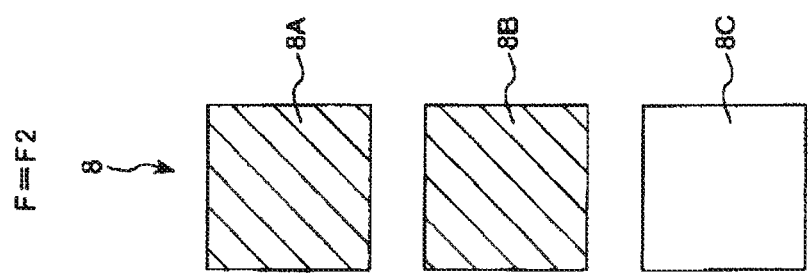
Figure 8A:
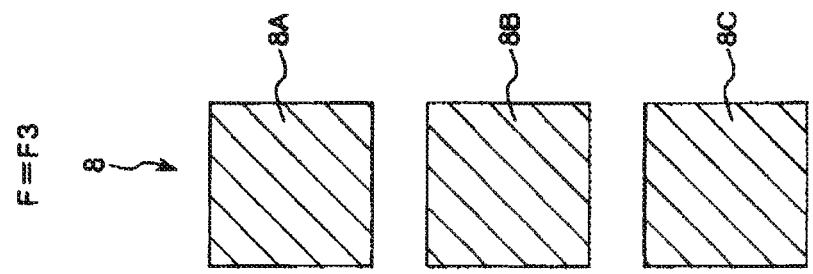

Then, as illustrated in FIG. 8(c), when the pressing force F reaches the third predetermined pressing force F3, the discoloration portion 8C is discolored. After the discoloration is confirmed, the supply of the fluid to the balloon 5 is stopped.

As described above, according to the present embodiment, while the strength level of the pressing force F applied from the balloon 5 to the puncture site 510 is recognized, the fluid can be supplied to the balloon 5. Therefore, the hemostasis can be more safely performed on the puncture site 510. In addition, it is also possible to correspond to patients who respectively have different blood pressures. Therefore, the hemostasis tool 1A is remarkably versatile.

In the present embodiment, the discoloration portions 8A to 8C are mounted on the hemostasis tool 1A in advance. However, without being limited thereto, the following forms may be employed.

For example, the hemostasis tool in a state where the discoloration portion is not mounted thereon and the respective discoloration portion 8A to 8C may be accommodated in a package or the like. When the hemostasis is performed, a patient's blood pressure is first measured. Then, it is recognized which discoloration portion is suitable for the patient's blood pressure. Next, the hemostasis tool is pulled out from the package, and the suitable discoloration portion is mounted on the hemostasis tool. Then, as described above, the hemostasis is performed.

Figures 12A, 12B:
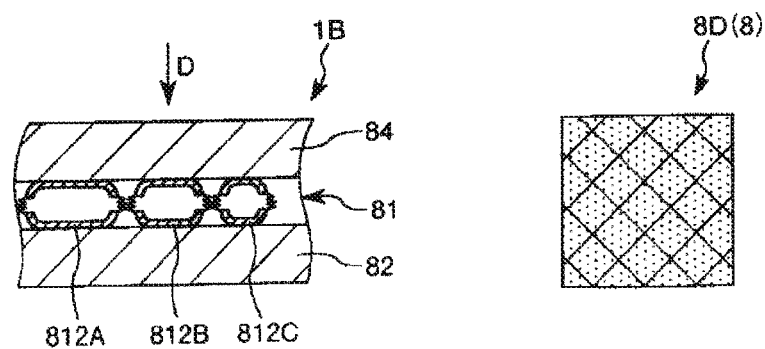
FIG. 12(a) is an enlarged sectional view illustrating a process in which the discoloration portion included in the third embodiment of the hemostasis tool according to the present disclosure is discolored.
FIG. 12(b) is a view when viewed in a direction of an arrow D in FIG. 12(a).

FIG. 9(a) is an enlarged sectional view illustrating a process in which a discoloration portion included in a third embodiment of a hemostasis tool according to the present disclosure is discolored, and FIG. 9(b) is a view when viewed in a direction of an arrow A in FIG. 9(a). FIG. 10(a) is an enlarged sectional view illustrating a process in which the discoloration portion included in the third embodiment of the hemostasis tool according to the present disclosure is discolored, and FIG. 10(b) is a view when viewed in a direction of an arrow B in FIG. 10(a). FIG. 11(a) is an enlarged sectional view illustrating a process in which the discoloration portion included in the third embodiment of the hemostasis tool according to the present disclosure is discolored, and FIG. 11(b) is a view when viewed in a direction of an arrow C in FIG. 11(a). FIG. 12(a) is an enlarged sectional view illustrating a process in which the discoloration portion included in the third embodiment of the hemostasis tool according to the present disclosure is discolored, and FIG. 12(b) is a view when viewed in a direction of an arrow D in FIG. 12(a).

Hereinafter, the third embodiment of the hemostasis tool according to the present disclosure will be described with reference to the drawings. However, points different from those in the above-described embodiments will be mainly described, and description of the same points will be omitted.

A hemostasis tool 1B according to the present embodiment is the same as that according to the second embodiment except that the configuration of the discoloration portions is different.

The color developer layer 81 of a discoloration portion 8D of the hemostasis tool 1B according to the present embodiment has three types of microcapsules 812A, 812B, and 812C which respectively have different sizes. In color developer layer 81, the respective microcapsules 812A to 812C are disposed densely, that is, so that the adjacent microcapsules 812 are in contact with each other. The respective microcapsules 812A adopt the same configuration. Accordingly, one representative microcapsule in the respective microcapsules 812A will be described. Similarly, representative microcapsules in the respective microcapsules 812B and 812C will be described one by one.

As illustrated in FIG. 9, the respective microcapsules 812A to 812C have the same wall thickness, but inner diameters and outer diameters (hereinafter, these will be simply referred to as a "size") are different from each other.

The microcapsule 812A is largest among the microcapsules 812A to 812C. In addition, a color developer 811A which is discolored from colorless to red by the acting from the developer 821 is included inside the microcapsule 812A. In a natural state, the microcapsule 812A is in contact with both the developer layer 82 and the second support layer 84. The microcapsule 812A configured in this way is broken when the pressing force F reaches the first predetermined pressing force F1.

The microcapsule 812B is smaller than the microcapsule 812A, and is larger than the microcapsule 812C. In addition, a color developer 811B which is discolored from colorless to blue by the acting from the developer 821 is included inside the microcapsule 812B. The microcapsule 812B is in contact with the developer layer 82, and is separated from the second support layer 84. The microcapsule 812B configured in this way is broken when the pressing force F reaches the second predetermined_pressing force F2.

The microcapsule 812C is smallest among the microcapsules 812A to 812C. In addition, a color developer 811C which is discolored from colorless to yellow by the acting from the developer 821 is included inside the microcapsule 812C. The microcapsule 812C is in contact with the developer layer 82, and is separated from the second support layer 84. A separated distance between the microcapsule 812C and the second support layer 84 is longer than a separated distance between the microcapsule 812B and the second support layer 84. The microcapsule 812C configured in this way is broken when the pressing force F reaches the third predetermined pressing force F3.

Next, a method of using the hemostasis tool 1B will be described. However, similarly to the second embodiment, when the pressing force F reaches the third predetermined pressing force F3, that is, when the microcapsule 812C is broken, it is considered that the pressing force F has suitable strength.

The hemostasis tool 1B is brought into a mounted state, and the balloon 5 is dilated. If the pressing force F increases and reaches the first predetermined pressing force F1, each microcapsule 812A is first broken (refer to FIG. 10(a)). In this manner, the color developer 811A is discolored to red (refer to FIG. 10(b)). As a result, the discoloration portion 8D is discolored to red.

If the balloon 5 is further dilated and the pressing force F reaches the second predetermined_pressing force F2, the microcapsule 812B is broken (refer to FIG. 11(a)). In this manner, the color developer 811B is discolored to blue. As a result, in the discoloration portion 8D, red and blue are mixed with each other, and the entire body is discolored from red to purple (refer to FIG. 11(b)).

When the balloon 5 is further dilated and the pressing force F reaches the third predetermined pressing force F3, the microcapsule 812C is broken (refer to FIG. 12(a)). In this manner, the color developer 811C is discolored to yellow. As a result, in the discoloration portion 8D, purple and yellow are mixed with each other, and the entire body is discolored from purple to black (brown) (refer to FIG. 12(b)). Since the discoloration is visible, it is possible to recognize that the pressing force F has suitable strength.

As described above, according to the present embodiment, similarly to the second embodiment, while the strength level of the pressing force F applied from the balloon 5 to the puncture site 510 is recognized, the fluid can be supplied to the balloon 5. Furthermore, a simple configuration is adopted in which only one discoloration portion 8D is mounted on the hemostasis tool 1B. In this manner, it is possible to correspond to patients who respectively have different blood pressures.

Figure 13A:
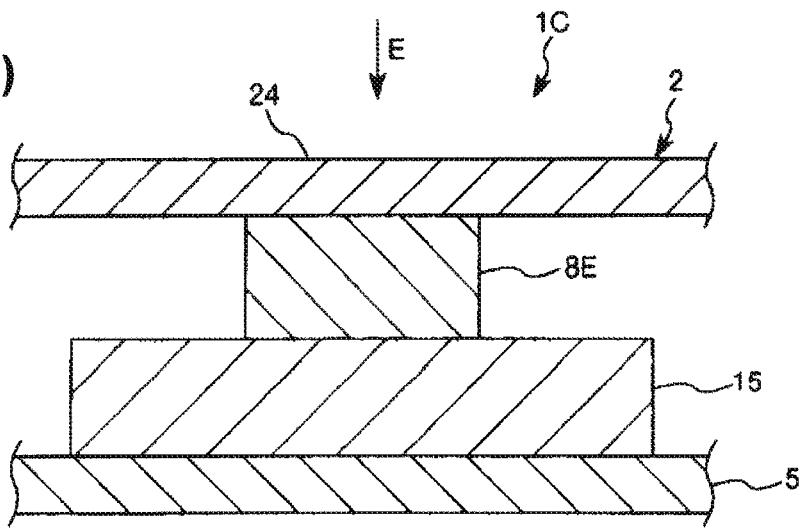
FIGS. 13(a) and 13(b) are enlarged sectional views illustrating a process in which a deformation portion included in a fourth embodiment of a hemostasis tool according to the present disclosure is deformed.
Figure 13B:
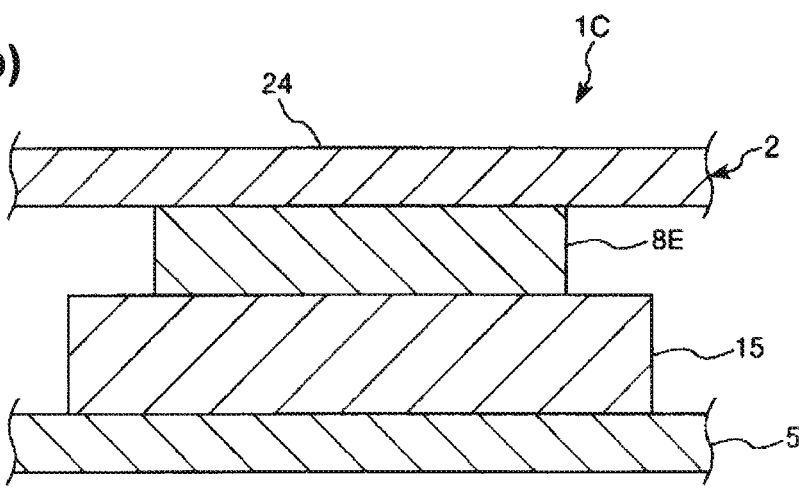
Figure 13C:
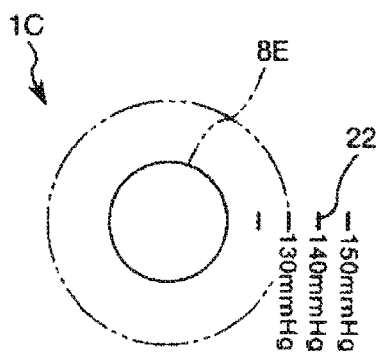
FIG. 13(c) is a view when viewed in a direction of an arrow E in FIG. 13(a).

FIGS. 13(a) and 13(b) are enlarged sectional views illustrating a process in which a deformation portion included in a fourth embodiment of a hemostasis tool according to the present disclosure is deformed, and FIG. 13(c) is a view when viewed in a direction of an arrow E in FIG. 13(a).

Hereinafter, the fourth embodiment of the hemostasis tool according to the present disclosure will be described with reference to the drawings. However, points different from those in the above-described embodiments will be mainly described, and description of the same points will be omitted.

A hemostasis tool 1C according to the present embodiment is substantially the same as that according to the second embodiment and the third embodiment except that the configuration of the detection unit is different.

As illustrated in FIGS. 13(a) to 13(c), in the present embodiment, the detection unit 8 of the hemostasis tool 1C is configured to include a deformation portion 8E which is deformed in response to the strength of the pressing force F. A configuration is adopted in which the strength level of the pressing force F is detected since a deformation amount of the deformation portion 8E is visible.

The deformation portion 8E is configured to include an elastic body having a disc shape. As illustrated in FIG. 10(b), if the pressing force F increases, the deformation portion 8E is crushed in the thickness direction of the bandage body 2 between the support piece 15 and the bandage body 2. In response to the strength of the pressing force F, the deformation portion 8E is elastically deformed so that the diameter increases in the surface direction of the bandage body 2.

In addition, as illustrated in FIG. 13(c), a scale (marker) 22 for indicating the strength level of the pressing force F corresponding to the deformation amount of the deformation portion 8E is disposed in a portion corresponding to the deformation portion 8E on an outer surface of the bandage body 2. The scale 22 is configured to include a color portion, and is disposed along the width direction of the bandage body 2. In this manner, it is possible to recognize the deformation amount of the deformation portion 8E at a glance.

In addition, for example, the scale 22 is marked together with a number (marker) at an interval of 5 mm. In the present embodiment, the number represents a patient's blood pressure indicating "130 mmHg", "140 mmHg", and "150 mmHg".

This hemostasis tool 1C is configured as follows. For example, as illustrated by a two-dot chain line in FIG. 13(c), when the scale 22 of the portion corresponding to "130 mmHg" and a portion of the contour of the deformation portion 8E overlap each other, the pressing force F for a patient whose blood pressure is 130 mmHg or lower is set to suitable strength (first predetermined pressing force F1).

Similarly, a configuration is adopted as follows. When the scale 22 of the portion corresponding to "140 mmHg" and the portion of the contour of the deformation portion 8E overlap each other, the pressing force F for a patient whose blood pressure is 131 mmHg to 140 mmHg is set to suitable strength (second predetermined_pressing force F2).

Similarly, a configuration is adopted as follows. When the scale 22 of the portion corresponding to "150 mmHg" and the portion of the contour of the deformation portion 8E overlap each other, the pressing force F for a patient whose blood pressure is 141 mmHg to 150 mmHg is set to suitable strength (third predetermined pressing force F3).

According to this configuration, it is possible to immediately recognize whether the pressing force F has the suitable strength, and it is possible to correspond to multiple patients who respectively have different blood pressures.

Here, when hemostasis is performed using the hemostasis tool 1C, in some cases, a patient's blood pressure varies. For example, in a case where the a patient's blood pressure increases in a state where the puncture site 510 of the patient whose blood pressure is 140 mmHg is compressed using the second predetermined pressing force F2, for example, in a case where the blood pressure varies from 140 mmHg to 150 mmHg, there is a possibility that the second predetermined-_pressing force F2 may be insufficient. However, while the hemostasis is performed, the patient's blood pressure is periodically measured. In this manner, it is possible to recognize that the blood pressure increases up to 150 mmHg. In this manner, the balloon 5 is dilated so that the scale 22 of the portion corresponding to "150 mmHg" and the portion of the contour of the deformation portion 8E overlap each other. Accordingly, the pressing force F can be set to the suitable strength (third predetermined pressing force F3).

On the other hand, in a case where the patient's blood pressure decreases, for example, in a case where the blood pressure decreases from 140 mmHg to 130 mmHg, there is a possibility that the second predetermined_pressing force F2 may be excessive. However, while the hemostasis is performed, the patient's blood pressure is periodically measured. In this manner, it is possible to recognize that the blood pressure decreases down to 130 mmHg. In this manner, the balloon 5 is deflated so that the scale 22 of the portion corresponding to "130 mmHg" and the portion of the contour of the deformation portion 8E overlap each other. Accordingly, the pressing force F can be set to the suitable strength (first predetermined pressing force F1).

Furthermore, in the middle of performing the hemostasis, there is a possibility that the bandage body 2 may be loosened. In a case where the bandage body 2 is loosened, the pressing force F decreases, and the diameter of the deformation portion 8E slightly decreases in the surface direction of the bandage body 2. Since the decreased diameter is visible, it is possible to recognize that the bandage body 2 is loosened. In this manner, the bandage body 2 is tightened again, or the fluid is supplied to the balloon 5. Accordingly, the pressing force F can restore the suitable strength.

In this way, the diameter of the detection unit 8 (deformation portion 8E) according to the present embodiment decreases after increasing once. Thereafter, the diameter increases again, that is, the diameter is reversibly deformed. Therefore, while the deformation amount of the deformation portion 8E is confirmed, the pressing force F can be adjusted. Furthermore, even after the hemostasis is completely performed and the hemostasis tool 1C is detached from the wrist, the deformation portion 8E can be reused by being mounted on another hemostasis tool or the like.

Figure 14A:
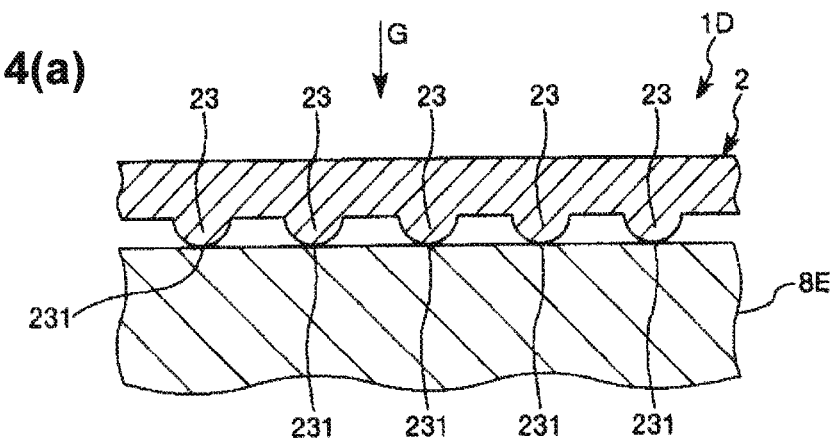
FIGS. 14(a) and 14(b) are enlarged sectional views illustrating a process in which a deformation portion included in a fifth embodiment of a hemostasis tool according to the present disclosure is deformed.
Figure 14B:
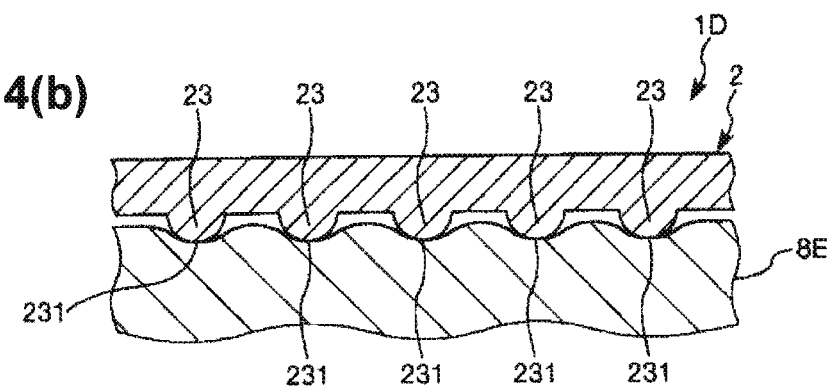
Figure 14C:
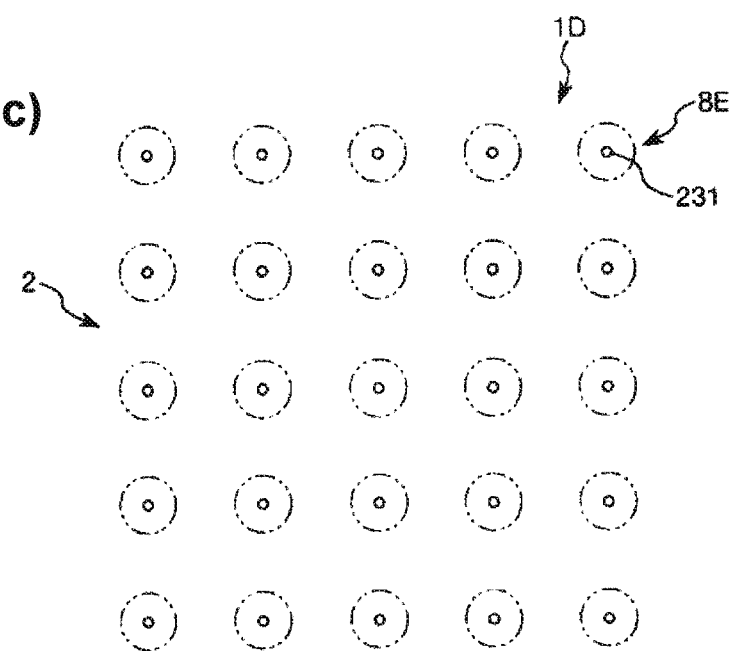
FIG. 14(c) is a view when viewed in a direction of an arrow G in FIG. 14(a).

FIGS. 14(a) and 14 (b) are enlarged sectional views illustrating a process in which a deformation portion included in a fifth embodiment of a hemostasis tool according to the present disclosure is deformed, and FIG. 14(c) is a view when viewed in a direction of an arrow G in FIG. 14(a).

Hereinafter, the fifth embodiment of the hemostasis tool according to the present disclosure will be described with reference to the drawings. However, points different from those in the above-described embodiments will be mainly described, and description of the same points will be omitted.

A hemostasis tool 1D according to the present embodiment is substantially the same as that according to the fourth embodiment except that the configuration of the bandage body is different.

As illustrated in FIGS. 14(a) to 14(c), in the hemostasis tool 1D according to the present disclosure, multiple projection portions 23 projecting inward are disposed on an inner side surface of the bandage body 2. The respective projection portions 23 have a semi-spherical shape, and are disposed while being arrayed in a grid shape. The respective projection portions 23 have the same configuration, and thus, one representative projection portion 23 thereof will be described.

In the projection portion 23, before the balloon 5 is dilated in a mounted state, an apex 231 closely adheres to (is in contact with) the deformation portion 8E. Other portions are separated from the deformation portion 8E. In a case where the deformation portion 8E is viewed from the outside of the bandage body 2 in this state, a portion closely adhering to the apex 231 of the deformation portion 8E is clearly visible, since an air layer is not interposed between the deformation portion 8E and the bandage body 2. On the other hand, a portion which does not closely adhere to the apex 231 of the deformation portion 8E is blurredly viewed, since the air layer is interposed between the deformation portion 8E and the bandage body 2.

Then, as illustrated in FIG. 14(b), if the balloon 5 is dilated, the deformation portion 8E is crushed while being deformed along a curved shape of the projection portion 23 between the bandage body 2 (projection portion 23) and the support piece 15. As a result, as illustrated by a two-dot chain line in FIG. 14(c), a contact area between the projection portion 23 and the deformation portion 8E increases. Since the size of the contact area is visible, it is possible to detect the strength level of the pressing force F.

According to the fifth embodiment, it is also possible to obtain an advantageous effect which is the same as that according to the fourth embodiment.

Hitherto, the hemostasis tool according to the present disclosure has been described with reference to the illustrated embodiments. However, the present disclosure is not limited thereto, and each element configuring the hemostasis tool can be replaced with any optional configuration which can fulfill the same function. In addition, any optional configuration may be added to the present disclosure.

For example, in the first embodiment, the discoloration portion 8A is irreversibly discolored. However, the present disclosure is not limited thereto, and the discoloration portion 8A may be reversibly discolored as in the fourth embodiment. In this manner, while the discoloration portion 8A is confirmed, the internal pressure of the balloon can be adjusted.

In addition, in the fourth embodiment, the deformation portion 8E is irreversibly deformed. However, the present disclosure is not limited thereto, and the deformation portion 8E may be reversibly deformed as in the first embodiment. In this manner, a user can obviously and reliably recognize that the deformation portion 8E is deformed.

Note that, the hemostasis tool according to the present disclosure is not limited to those which are used by being mounted on the wrist. The present disclosure is also applicable to a hemostasis tool which is used by being mounted on any other part of the arm or the leg (herein, these are collectively referred to as the "limb").

In addition, in the first embodiment, the discoloration portion 8A is discolored from colorless to red. However, the present disclosure is not limited thereto. For example, as long as the color change is visible, the discoloration portion 8A may be discolored from white to red or from red to colorless without being limited thereto.

In addition, in the second embodiment, the respective discoloration portions are arrayed along the width direction of the bandage body. However, the present disclosure is not limited thereto. For example, the respective discoloration portions may be arrayed along the longitudinal direction of the bandage body. In addition, the respective discoloration portions may be arranged side by side while being tilted in the width direction and the longitudinal direction of the bandage body. Furthermore, the respective discoloration portions may not be arrayed.

In addition, in the second embodiment, the detection unit has three discoloration portions. However, the present disclosure is not limited thereto. For example, the detection unit may have two discoloration portions, and alternatively four or more.

In addition, in the fifth embodiment, the shape of the projection portion is the semi-spherical shape. However, the present disclosure is not limited thereto. For example, even if the projection portion has any shape such as a rib shape extending in one direction, a ring shape, a prismatic shape, and the like, it is possible to achieve an advantageous effect which is the same as the advantageous effect according to the present disclosure.

In addition, in the respective embodiments, the overall bandage body is the light-transmitting portion. However, the present disclosure is not limited thereto. At least a portion corresponding to the detection unit of the bandage body may be the light-transmitting portion.

A hemostasis tool according to the present disclosure has a flexible bandage body that is used by being wound around a site requiring hemostasis, at least one balloon that is installed in the bandage body, and that is dilated by injecting a fluid so as to compress the site requiring hemostasis in a dilated state thereof, and a detection unit that detects a strength level of a pressing force of the balloon pressing the site requiring hemostasis, based on discoloration or deformation. Therefore, the detection unit can detect the pressing force of the balloon compressing the site requiring hemostasis. Accordingly, the balloon can properly compress the site requiring hemostasis.

The detailed description above describes a hemostasis tool. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostasis tool comprising:
a flexible bandage body that is configured to be wound around a site requiring hemostasis;
a balloon that is arranged in the bandage body, and is configured to be dilated by injecting a fluid so as to compress the site requiring hemostasis in a dilated state thereof;
a detection unit that is configured to detect a strength level of a pressing force of the balloon pressing the site requiring hemostasis, based on discoloration or deformation;
an auxiliary balloon configured to press against the balloon when the balloon is dilated;
a pair of pinching pieces which are configured to pinch the detection unit when the flexible bandage body is wound around the site requiring hemostasis and the balloon is dilated, the pair of pinching pieces being harder than the detection unit, an inner piece of the pair of pinching pieces being disposed between the balloon and the detection unit, and the auxiliary balloon being disposed between the balloon and an outer piece of the pair of pinching pieces.

2. The hemostasis tool according to claim 1,
wherein the bandage body has a light-transmitting portion having light transmittance, and
wherein the detection unit is located between the balloon and the light-transmitting portion, and is visible via the light-transmitting portion.

3. The hemostasis tool according to claim 2,
wherein the detection unit has a deformation portion which is configured to deform in response to the strength of the pressing force, and which detects the strength level of the pressing force, based on a deformation amount thereof.

4. The hemostasis tool according to claim 3,
wherein the deformation portion is arranged so as to face the light-transmitting portion, and is configured to dilate in a plane direction of the bandage body in response to the strength of the pressing force.

5. The hemostasis tool according to claim 1,
wherein the detection unit has a discoloration portion which is irreversibly discolored due to an increase in the pressing force.

6. The hemostasis tool according to claim 5,
wherein the discoloration portion has a color developer, a developer which develops a color of the color developer by acting on the color developer, and a partition wall portion which separates the color developer and the developer, and which is configured to be broken due to the increase in the pressing force.

7. The hemostasis tool according to claim 6,
further comprising a second partition wall portion having a breaking limit different than a breaking limit of the first wall portion.

8. The hemostasis tool according to claim 1,
wherein the detection unit has a deformation portion which is configured to deform in response to the strength of the pressing force, and which detects the strength level of the pressing force, based on a deformation amount thereof.

9. The hemostasis tool according to claim 8, further comprising:
a scale or a marker that indicates the strength level of the pressing force in response to the deformation amount of the deformation portion.

10. The hemostasis tool according to claim 1,
wherein the detection unit is arranged at a position shifted from a straight line passing through the center of the balloon in the dilated state and the site requiring hemostasis.

* * * * *